(12) United States Patent
Ishibashi et al.

(10) Patent No.: US 7,220,430 B2
(45) Date of Patent: May 22, 2007

(54) SUSTAINED-RELEASE PREPARATION AND PROCESS FOR PRODUCING THE SAME

(75) Inventors: Takashi Ishibashi, Sakai (JP); Kengo Ikegami, Nishinomiya (JP); Keigo Nagao, Kawanishi (JP); Hiroyuki Yoshino, Suita (JP); Masakazu Mizobe, Takatsuki (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 625 days.

(21) Appl. No.: 10/182,239

(22) PCT Filed: Jan. 26, 2001

(86) PCT No.: PCT/JP01/00502

§ 371 (c)(1),
(2), (4) Date: Jul. 25, 2002

(87) PCT Pub. No.: WO01/54671

PCT Pub. Date: Aug. 2, 2001

(65) Prior Publication Data

US 2003/0012815 A1     Jan. 16, 2003

(30) Foreign Application Priority Data

Jan. 27, 2000   (JP)   ............................. 2000-018323

(51) Int. Cl.
| | | |
|---|---|---|
| A61K 9/24 | (2006.01) | |
| A61K 9/22 | (2006.01) | |
| A61K 9/28 | (2006.01) | |
| A61K 9/30 | (2006.01) | |
| A61K 9/42 | (2006.01) | |

(52) U.S. Cl. ...................... 424/472; 424/468; 424/474; 424/475; 424/476

(58) Field of Classification Search ................ 424/468, 424/472, 474, 475, 476
See application file for complete search history.

(56) References Cited

U.S. PATENT DOCUMENTS

| 4,359,483 A | 11/1982 | Kaetsu et al. |
|---|---|---|
| 4,863,742 A * | 9/1989 | Panoz et al. |
| 5,296,236 A | 3/1994 | Santus et al. |
| 5,447,729 A | 9/1995 | Belenduik et al. |
| 5,527,545 A | 6/1996 | Santus et al. |
| 5,674,533 A | 10/1997 | Santus et al. |

FOREIGN PATENT DOCUMENTS

EP        0 320 097 A1    6/1989

(Continued)

Primary Examiner—Humera N Sheikh
(74) Attorney, Agent, or Firm—Birch, Stewart, Kolasch & Birch, LLP (57) ABSTRACT

The present invention is to provide a sustained release preparation comprising a drug-containing core substance and a multilayered coating layer covering the core substance, wherein all adjacent layers in the multilayered coating layer contain mutually different hydrophobic organic compound-water-soluble polymer mixtures; and, a method of producing a sustained release preparation, having a multilayered coating layer in which adjacent layers contain different hydrophobic organic compound-water-soluble polymer mixtures, which comprises spray-coating a solution containing a hydrophobic organic compound-water-soluble polymer mixture onto a drug-containing core substance, continuing to spray-coat a solution containing a different hydrophobic organic compound-water-soluble polymer mixture onto the resulting coating layer, and repeating this step.

21 Claims, 5 Drawing Sheets

FOREIGN PATENT DOCUMENTS

| | | |
|---|---|---|
| EP | 0 335 560 A2 | 10/1989 |
| EP | 0 438 249 A1 | 7/1991 |
| EP | 0 671 168 A1 | 9/1995 |
| GB | 2 245 492 A | 1/1992 |
| JP | 4-290817 A | 10/1992 |
| WO | 92/20326 A1 | 11/1992 |
| WO | 95/25506 A1 | 9/1995 |

* cited by examiner

SUSTAINED-RELEASE PREPARATION AND PROCESS FOR PRODUCING THE SAME

This application is the national phase under 35 U.S.C. § 371 of PCT International Application No. PCT/JP01/00502 which has an International filing date of Jan. 26, 2001, which designated the United States of America.

1. Field of the Invention

The present invention relates to a sustained release preparation and a method for producing the same, and more particularly to a sustained release preparation which is able to control the drug release efficiently over the long period of time with a small coating amount, without causing a phenomenon of reaching the upper limit of drug release, thereby making it possible to release the drug continuously even at the lower portion of a digestive tract having small moisture content, and a method for producing the same.

2. Background Art

As an oral sustained release preparation, one that comprises a drug-containing core substance coated with a water-insoluble coating material has been known. Such a preparation is advantageous in that the drug is continuously released; however, it has a problem that the drug releasing rate is lowered in the course of time, so that the drug is not released completely, that is, a phenomenon of reaching the upper limit of drug release (see Japanese Unexamined Patent Publication No. 7-196477).

For example, when the coating amount is so small that the time required for 50% of the drug in the preparation to be released (T50%) is about 1 hour, almost all the drug is released. However, for a preparation to be taken once per day, having an increased coating amount such that the T50% is 6 to 10 hours, the amount of the drug released 20 hours after the start of releasing (D20h) only reaches about 60% in many cases. Further, in the case of using a drug which is hard to be dissolved, it is often recognized that the D20h is 60% or less. Such a phenomenon of reaching the upper limit of drug release is unfavorable for preparations because it causes the bioavailability to be lowered. On the other hand, in the case of an extremely highly water soluble drug, the above phenomenon of reaching the upper limit of drug release is unlikely to occur. However, in order to suppress the rate of drug release, a large amount of coating is required. For this reason, this kind of drug requires a very long time for coating, thereby having a disadvantage in production efficiency, and further, a preparation with high drug content cannot be obtained.

In addition, in case of an oral sustained release preparation wherein the drug is absorbed while the preparation moves down through a digestive tract, the drug can be well released in the upper portion of the digestive tract having large moisture content. However, in the lower portion of the digestive tract having small moisture content, the absorption of the drug often becomes unsatisfactory since the release of the drug is suppressed. Even though a preparation can be obtained that can release a drug at a constant rate for 24 hours in an in vitro dissolution test, it does not necessarily mean that the preparation obtained can prolong a pharmacological effect of the drug for 24 hours.

Therefore, with the conventional coating with a water-insoluble coating material, it has been very difficult to obtain a sustained release preparation that can be taken once per day.

The object of the present invention is to provide a sustained release preparation which is able to control the drug release efficiently over the long period of time with a small coating amount, without causing a phenomenon of reaching the upper limit of drug release, thereby making it possible to release the drug continuously even at the lower portion of a digestive tract having small moisture content, and a method for producing the same.

SUMMARY OF THE INVENTION

The present inventors have made extensive and intensive studies with a view toward solving the above-mentioned problems. As a result, they have found that, when a drug-containing core substance is coated with a multilayered coating layer having a construction such that the adjacent layers contain mutually different hydrophobic organic compound-water-soluble polymer mixtures, the preparation can efficiently control the drug release for a long period of time, hardly leading to an unfavorable phenomenon of reaching the upper limit of drug release and thus, the present invention has been completed.

Further, when the preparation of the present invention is orally administered, the multilayered coating layer undergoes erosion and slowly becomes thinner in the course of time, namely, while the preparation moves through a digestive tract. Therefore, the preparation also has an excellent effect of releasing the drug satisfactorily even in the lower portion of a digestive tract having small moisture content.

Namely, the present invention relates to a sustained release preparation which comprises a drug-containing core substance and a multilayered coating layer covering the core substance, wherein all the adjacent layers in the multilayered coating layer contain mutually different hydrophobic organic compound-water-soluble polymer mixtures.

Further, the present invention relates to a method for producing a sustained release preparation having a multilayered coating layer in which the adjacent layers in the multilayered coating layer contain mutually different hydrophobic organic compound-water-soluble polymer mixtures which comprises spray-coating a solution containing a hydrophobic organic compound-water-soluble polymer mixture onto a drug-containing core substance, continuing to spray-coat a solution containing a different hydrophobic organic compound-water-soluble polymer mixture onto the resulting coating layer, and repeating this step.

BEST MODE FOR CARRYING OUT THE INVENTION

The layers in the multilayered coating layer of the preparation of the present invention individually comprise a layer containing a hydrophobic organic compound-water-soluble polymer mixture, and the adjacent layers in the multilayered coating layer contain mutually different hydrophobic organic compound-water-soluble polymer mixtures.

The hydrophobic organic compound in the present invention is a hydrophobic organic compound that is not in the form of a salt and excludes a polymer. Examples of hydrophobic organic compounds used in the layer containing a hydrophobic organic compound-water-soluble polymer mixture include higher fatty acids having 6 to 22 carbon atoms that may or may not have an unsaturated bond, higher alcohols having 6 to 22 carbon atoms that may or may not have an unsaturated bond, triglycerides of higher fatty acids having 6 to 22 carbon atoms that may or may not have an unsaturated bond, natural fats and oils that may or may not be hydrogenated, and the like.

Examples of higher fatty acids having 6 to 22 carbon atoms that may or may not have an unsaturated bond include stearic acid, lauric acid, myristic acid, palmitic acid, behenic acid, and the like. Examples of higher alcohols having 6 to 22 carbon atoms that may or may not have an unsaturated bond include lauryl alcohol, myristyl alcohol, cetyl alcohol, stearyl alcohol, behenyl alcohol, and the like. Examples of triglycerides of higher fatty acids having 6 to 22 carbon atoms that may or may not have an unsaturated bond include triglycerides of the above-mentioned higher fatty acids, such as stearic acid triglyceride, myristic acid triglyceride, palmitic acid triglyceride, lauric acid triglyceride, and the like. Examples of natural fats and oils that may or may not be hydrogenated include hydrogenated castor oil, hydrogenated coconut oil, beef tallow, and the like. Of these, especially preferred are stearic acid and palmitic acid, and most preferred is stearic acid.

These hydrophobic organic compounds may be used individually or in combination of two or more kinds.

Examples of water-soluble polymer substances used in the layer containing a hydrophobic organic compound-water-soluble polymer mixture include a water-soluble cellulose ether, a water-soluble polyvinyl derivative, an alkylene oxide polymer, and the like.

Examples of water-soluble cellulose ethers include methyl cellulose, hydroxypropyl cellulose, hydroxypropyl methyl cellulose, and the like; examples of water-soluble polyvinyl derivatives include polyvinylpyrrolidone, polyvinyl alcohol, and the like; and examples of alkylene oxide polymers include polyethylene glycol, polypropylene glycol, and the like. Of these, especially preferred is hydroxypropyl cellulose.

These water-soluble polymers may be used individually or in combination of two or more kinds.

In the hydrophobic organic compound-water-soluble polymer mixture, preferred examples of combinations of the hydrophobic organic compound and the water-soluble polymer include a combination of a higher fatty acid having 6 to 22 carbon atoms that may or may not have an unsaturated bond and a water-soluble cellulose ether (e.g., stearic acid-hydroxypropyl cellulose, palmitic acid-hydroxypropyl cellulose, lauric acid-hydroxy-propyl cellulose, myristic acid-hydroxypropyl cellulose, behenic acid-hydroxypropyl cellulose, or the like); a combination of a higher fatty acid having 6 to 22 carbon atoms that may or may not have an unsaturated bond and a water-soluble polyvinyl derivative (e.g., stearic acid-polyvinylpyrrolidone, palmitic acid-polyvinylpyrrolidone, lauric acid-polyvinylpyrrolidone, myristic acid-polyvinylpyrrolidone, behenic acid-polyvinylpyrrolidone, or the like); a combination of a higher fatty acid having 6 to 22 carbon atoms that may or may not have an unsaturated bond and an alkylene oxide polymer (e.g., stearic acid-polyethylene glycol, palmitic acid-polyethylene glycol, lauric acid-polyethylene glycol, myristic acid-polyethylene glycol, behenic acid-polyethylene glycol, or the like); a combination of a higher alcohol having 6 to 22 carbon atoms that may or may not have an unsaturated bond and a water-soluble cellulose ether (e.g., stearyl alcohol-hydroxy-propyl cellulose, lauryl alcohol-hydroxypropyl cellulose, myristyl alcohol-hydroxypropyl cellulose, cetyl alcohol-hydroxypropyl cellulose, behenyl alcohol-hydroxypropyl cellulose, or the like); a combination of a higher alcohol having 6 to 22 carbon atoms that may or may not have an unsaturated bond and a water-soluble polyvinyl derivative (e.g., stearyl alcohol-polyvinylpyrrolidone, lauryl alcohol-polyvinylpyrrolidone, myristyl alcohol-polyvinylpyrrolidone, cetyl alcohol-polyvinylpyrrolidone, behenyl alcohol-polyvinylpyrrolidone, or the like); a combination of a higher alcohol having 6 to 22 carbon atoms that may or may not have an unsaturated bond and an alkylene oxide polymer (e.g., stearyl alcohol-polyethylene glycol, lauryl alcohol-polyethylene glycol, myristyl alcohol-polyethylene glycol, cetyl alcohol-polyethylene glycol, behenyl alcohol-polyethylene glycol, or the like); a combination of a triglyceride of a higher fatty acid having 6 to 22 carbon atoms that may or may not have an unsaturated bond and a water-soluble cellulose ether (e.g., stearic acid triglyceride-hydroxypropyl cellulose, myristic acid tri-glyceride-hydroxypropyl cellulose, palmitic acid triglyceride-hydroxypropyl cellulose, lauric acid triglyceride-hydroxy-propyl cellulose, or the like); a combination of a triglyceride of a higher fatty acid having 6 to 22 carbon atoms that may or may not have an unsaturated bond and a water-soluble polyvinyl derivative (e.g., stearic acid triglyceride-polyvinylpyrrolidone, myristic acid triglyceride-polyvinylpyrrolidone, palmitic acid triglyceride-polyvinylpyrrolidone, lauric acid triglyceride-polyvinylpyrrolidone, or the like); a combination of a triglyceride of a higher fatty acid having 6 to 22 carbon atoms that may or may not have an unsaturated bond and an alkylene oxide polymer (e.g., stearic acid triglyceride-polyethylene glycol, myristic acid triglyceride-polyethylene glycol, palmitic acid triglyceride-polyethylene glycol, lauric acid triglyceride-polyethylene glycol, or the like); a combination of a natural fat or oil that may or may not be hydrogenated and a water-soluble cellulose ether (e.g., hydrogenated castor oil-hydroxypropyl cellulose, hydrogenated coconut oil-hydroxypropyl cellulose, beef tallow-hydroxypropyl cellulose, or the like); a combination of a natural fat or oil that may or may not be hydrogenated and a water-soluble polyvinyl derivative (e.g., hydrogenated castor oil-polyvinylpyrrolidone, hydrogenated coconut oil-polyvinylpyrrolidone, beef tallow-polyvinylpyrrolidone, or the like); a combination of a natural fat or oil that may or may not be hydrogenated and an alkylene oxide polymer (e.g., hydrogenated castor oil-polyethylene glycol, hydrogenated coconut oil-polyethylene glycol, beef tallow-polyethylene glycol, or the like); and mixtures obtained by optionally mixing together the above-mentioned hydrophobic organic compound-water-soluble polymer mixtures.

In the present invention, with respect to the content of the hydrophobic organic compound in the hydrophobic organic compound-water-soluble polymer mixture contained in each layer of the multilayered coating layer {% by weight; (hydrophobic organic compound)/(hydrophobic organic compound+water–soluble polymer)×100}, there is no particular limitation, but it is preferred that the content is in the range of from 20 to 99.5% by weight.

When the core substance has a large surface area per unit weight, such as a fine particle with an average particle diameter of 200 μm or less, it is difficult to suppress the dissolution. In such a case, in order to reduce the coating amount, it is preferred to select a hydrophobic organic compound content such that an effect of suppressing the drug release is expected to a certain extent even when it is used as a single layer. The hydrophobic organic compound content in this case varies depending on the types of the hydrophobic organic compound and water-soluble polymer used, but is generally in the range of from 80 to 99.5% by weight, especially preferably from 85 to 99% by weight.

On the other hand, when the core substance has an average particle diameter of 700 μm or more, for example, a granule, a tablet, a capsule, or the like, the surface area per unit weight of the core substance is relatively small, making it possible to suppress the drug release in a small coating ratio, as compared to the fine particles. In addition, by intentionally using the hydrophobic organic compound-water-soluble polymer mixture having a poor effect of suppressing the drug release to increase the coating amount, it is attempted to enhance the strength of the preparation and to prevent the deviation of the coating amount. Therefore, the hydrophobic organic compound content is generally in the range of from 20 to 80% by weight, being more preferably in the range of from 40 to 80% by weight.

Further, the layer containing a hydrophobic organic compound-water-soluble polymer mixture may comprises only a hydrophobic organic compound-water-soluble polymer mixture, but also may contain various additives in addition to the hydrophobic organic compound-water-soluble polymer mixture. Examples of such additives include a coloring agent, an opacifying agent, a plasticizer, a lubricant, and the like.

Examples of the coloring agents include a food dye, a lake dye, caramel, carotene, annatto, cochineal, iron sesquioxide, an opacifying coloring agent OPALUX comprised mainly of a lake dye and a syrup, and the like, and specific examples include food aluminum lake, such as food red No. 2, food red No. 3, food yellow No. 4, food yellow No. 5, food green No. 3, food blue No. 1, food blue No. 2, food purple No. 1, or the like, annatto (natural dye derived from annatto), carmine (aluminum carminate), pearl essence (composed essentially of guanine), and the like.

Examples of opacifying agents include titanium dioxide, precipitated calcium carbonate, calcium hydrogen phosphate, calcium sulfate, and the like.

Examples of plasticizers include phthalic acid derivatives, such as diethyl phthalate, dibutyl phthalate, butylphthalyl butyl glycolate, and the like; silicone oil; triethyl citrate; triacetin; propylene glycol; polyethylene glycol; and the like.

Examples of lubricants include magnesium stearate, talc, synthesized magnesium silicate, particulate silicon oxide, and the like.

With respect to the amounts of the above additives used, there is no particular limitation as long as the amounts fall within the range generally employed in the field of the preparation.

In the preparation of the present invention, the adjacent layers in the multilayered coating layer contain mutually different hydrophobic organic compound-water-soluble polymer mixtures, and the case wherein the adjacent layers in the multilayered coating layer contain mutually different hydrophobic organic compound-water-soluble polymer mixtures includes: (A) the case where the adjacent layers contain hydrophobic organic compound-water-soluble polymer mixtures in which at least one kind of either the hydrophobic organic compound or the water-soluble polymer is mutually different; and (B) the case where the adjacent layers contain hydrophobic organic compound-water-soluble polymer mixtures in which the kinds of the hydrophobic organic compound and the water-soluble polymer are the same, while the contents of the hydrophobic organic compound are mutually different.

In the case (A) above, in the comparison of the hydrophobic organic compound-water-soluble polymer mixtures contained in the adjacent layers, there can be mentioned the case where only the kinds of the hydrophobic organic compound is mutually different, the case where only the kinds of the water-soluble polymer is different, and the case where both kinds of the hydrophobic organic compound and the water-soluble polymer are mutually different.

In the case (A) above, the case where the kind of the water-soluble polymer is mutually different includes the case where the name of the water-soluble polymer is the same but the molecular weights thereof are different. In the present specification, when the components have the same name, that means they have the same molecular weights unless otherwise specified.

Specific examples of the combinations of the adjacent layers in which only the kinds of the water-soluble polymers are mutually different include a combination of a layer containing a stearic acid-hydroxypropyl cellulose mixture and a layer containing a stearic acid-polyvinylpyrrolidone mixture, a combination of a layer containing a palmitic acid-hydroxypropyl cellulose mixture and a layer containing a palmitic acid-polyvinylpyrrolidone mixture, a combination of a layer containing a stearic acid-palmitic acid-hydroxypropyl cellulose mixture and a layer containing a stearic acid-palmitic acid-polyvinylpyrrolidone mixture, a combination of a layer containing a stearic acid-hydroxypropyl cellulose mixture and a layer containing a stearic acid-polyethylene glycol mixture, a combination of a layer containing a palmitic acid-hydroxypropyl cellulose mixture and a layer containing a palmitic acid-polyethylene glycol mixture, a combination of a layer containing a stearic acid-palmitic acid-hydroxypropyl cellulose mixture and a layer containing a stearic acid-palmitic acid-polyethylene glycol mixture, and the like. Specific examples of the combinations of the adjacent layers in which only the kinds of the hydrophobic organic compounds are mutually different include a combination of a layer containing a stearic acid-hydroxypropyl cellulose mixture and a layer containing a palmitic acid-hydroxypropyl cellulose mixture, a combination of a layer containing a stearic acid-polyvinylpyrrolidone mixture and a layer containing a palmitic acid acid-polyvinylpyrrolidone mixture, a combination of a layer containing a stearic acid-polyethylene glycol mixture and a layer containing a palmitic acid-polyethylene glycol mixture, and the like. Specific examples of the combinations of the adjacent layers in which both kinds of the hydrophobic organic compounds and the water-soluble polymers are mutually different include a combination of a layer containing a stearic acid-hydroxypropyl cellulose mixture and a layer containing a palmitic acid-polyvinylpyrrolidone mixture, a combination of a layer containing a stearic acid-polyvinylpyrrolidone mixture and a layer containing a palmitic acid-hydroxypropyl cellulose mixture, a combination of a layer containing a stearic acid-hydroxypropyl cellulose mixture and a layer containing a palmitic acid-polyethylene glycol mixture, a combination of a layer containing a stearic acid-polyethylene glycol mixture and a layer containing a palmitic acid-hydroxypropyl cellulose mixture, and the like.

In the case (B) above, in the comparison of the hydrophobic organic compound-water-soluble polymer mixtures contained in the adjacent layers, the kinds of the hydrophobic organic compound and the water-soluble polymer are the same, while the contents of the hydrophobic organic compound are mutually different. The difference in the contents of the hydrophobic organic compound (% by weight) between the mixtures varies depending on the kinds of the mixtures, and generally, is preferably in the range of from 5 to 50% by weight, more preferably from 5 to 20% by weight.

Specific examples of the combinations of the adjacent layers in such a case include a combination of a layer containing a stearic acid-hydroxypropyl cellulose mixture having a stearic acid content of 98% by weight and a layer containing the same mixture having a stearic acid content of 90% by weight, a combination of a layer containing a stearic acid-hydroxypropyl cellulose mixture having a stearic acid content of 90% by weight and a layer containing the same mixture having a stearic acid content of 85% by weight, a combination of a layer containing a stearic acid-hydroxypropyl cellulose mixture having a stearic acid content of 98% by weight and a layer containing the same mixture having a stearic acid content of 85% by weight, a combination of a layer containing a palmitic acid-hydroxypropyl cellulose mixture having a palmitic acid content of 98% by weight and a layer containing the same mixture having a palmitic acid content of 90% by weight, a combination of a layer containing a palmitic acid-hydroxypropyl cellulose mixture having a palmitic acid content of 90% by weight and a layer containing the same mixture having a palmitic acid content of 85% by weight, a combination of a layer containing a stearic acid-polyethylene glycol mixture having a stearic acid content of 90% by weight and a layer containing the same mixture having a stearic acid content of 98% by weight, and the like.

In the present invention, the multilayered coating layer may be constituted so that all the adjacent layers are as in the case (A) above, that is, so that all the adjacent layers in the multilayered coating layer contain hydrophobic organic compound-water-soluble polymer mixtures in which at least one kind of either the hydrophobic organic compound or the water-soluble polymer is mutually different, or may be constituted so that all the adjacent layers are as in the case (B) above, that is, so that all the adjacent layers in the multilayered coating layer contain hydrophobic organic compound-water-soluble polymer mixtures in which the kinds of the hydrophobic organic compound and the water-soluble polymer are the same, while the contents of the hydrophobic organic compound are mutually different, or may be constituted so that the case (A) and the case (B) coexist, that is, so that the part of the adjacent layers in the multilayered coating layer contain hydrophobic organic compound-water-soluble polymer mixtures in which at least one kind of either the hydrophobic organic compound or the water-soluble polymer is mutually different, and the remaining adjacent layers contain hydrophobic organic compound-water-soluble polymer mixtures in which the kinds of hydrophobic organic compound and the water-soluble polymer are the same, while the contents of the hydrophobic organic compound are mutually different.

Further, in the preparation of the present invention, the multilayered coating layer has either only one combination or a plurality of combinations of the hydrophobic organic compound-water-soluble polymer mixtures contained in the adjacent layers.

When all the adjacent layers in the multilayered coating layer are constituted as in the case (A) above and, there is only one combination, in one preparation, of the hydrophobic organic compound-water-soluble polymer mixtures contained in the adjacent layers, specific examples of such multilayered coating layers include a multilayered coating layer comprising a layer containing a stearic acid-hydroxypropyl cellulose mixture and a layer containing a stearic acid-polyvinylpyrrolidone mixture, both of which are alternately laminated; a multilayered coating layer comprising a layer containing a stearic acid-hydroxypropyl cellulose mixture and a layer containing a stearic acid-polyethylene glycol mixture, both of which are alternately laminated; a multilayered coating layer comprising a layer containing a palmitic acid-hydroxypropyl cellulose mixture and a layer containing a palmitic acid-polyvinylpyrrolidone mixture, both of which are alternately laminated; a multilayered coating layer comprising a layer containing a palmitic acid-hydroxypropyl cellulose mixture and a layer containing a stearic acid-hydroxypropyl cellulose mixture, both of which are alternately laminated; and the like.

When all the adjacent layers in the multilayered coating layer are constituted as in the case (A) above and there are a plurality of combinations, in one preparation, of the hydrophobic organic compound-water-soluble polymer mixtures contained in the adjacent layers, specific examples of multilayered-coating layers include a multilayered coating layer comprising a layer containing a stearic acid-hydroxypropyl cellulose mixture, a layer containing a stearic acid-polyvinylpyrrolidone mixture, and a layer containing a palmitic acid-hydroxypropyl cellulose mixture; a multilayered coating layer comprising a layer containing a stearic acid-hydroxypropyl cellulose mixture, a layer containing a stearic acid-polyethylene glycol mixture, and a layer containing a palmitic acid-hydroxypropyl cellulose mixture; and the like.

When all the adjacent layers in the multilayered coating layer are constituted as in the case (B) above and, there is only one combination, in one preparation, of the hydrophobic organic compound-water-soluble polymer mixtures contained in the adjacent layers, specific examples of the multilayered coating layers include a multilayered coating layer comprising a layer containing a stearic acid-hydroxypropyl cellulose mixture having a stearic acid content of 98% by weight and a layer containing the same mixture having a stearic acid content of 85% by weight, both of which are alternately laminated; a multilayered coating layer comprising a layer containing a stearic acid-hydroxypropyl cellulose mixture having a stearic acid content of 98% by weight and a layer containing the same mixture having a stearic acid content of 90% by weight, both of which are alternately laminated; a multilayered coating layer comprising a layer containing a stearic acid-hydroxypropyl cellulose mixture having a stearic acid content of 90% by weight and a layer containing the same mixture having a stearic acid content of 85% by weight, both of which are alternately laminated; a multilayered coating layer comprising a layer containing a stearic acid-polyethylene glycol mixture having a stearic acid content of 90% by weight and a layer containing the same mixture having a stearic acid content of 98% by weight, both of which are alternately laminated; and the like.

When all the adjacent layers in the multilayered coating layer are constituted as in the case (B) above and, there are a plurality of combinations, in one preparation, of the hydrophobic organic compound-water-soluble polymer mixtures contained in the adjacent layers, specific examples of the multilayered coating layers include: (a) a multilayered coating layer having a layout such that the inner the layer in the multilayered coating layer, the higher the content of the hydrophobic organic compound of the hydrophobic organic compound-water-soluble polymer mixture contained, i.e., the outer the layer in the multilayered coating layer, the lower the content of the hydrophobic organic compound (for example, a multilayered coating layer comprising a layer containing a stearic acid-hydroxypropyl cellulose mixture having a stearic acid content of 98% by weight, a layer containing the same mixture having a stearic acid content of 90% by weight, and a layer containing the same mixture having a stearic acid content of 85% by weight, which layers are laminated in this order from inner layer); (b) a multilayered coating layer having a layout such that the inner the layer in the multilayered coating layer, the lower the content of the hydrophobic organic compound of the hydrophobic organic compound-water-soluble polymer mixture contained, i.e., the outer the layer in the multilayered coating layer, the higher the content of the hydrophobic organic compound (for example, a multilayered coating layer comprising a layer containing a stearic acid-hydroxypropyl cellulose mixture having a stearic acid content of 85% by weight, a layer containing the same mixture having a stearic acid content of 90% by weight, and a layer containing the same mixture having a stearic acid content of 98% by weight, which layers are laminated in this order from inner layer); (c) a multilayered coating layer having a layout such that the layers containing the hydrophobic organic compound-water-soluble polymer mixtures having mutually different contents of the hydrophobic organic compound are randomly laminated (for example, a multilayered coating layer comprising a layer containing a stearic acid-hydroxypropyl cellulose mixture having a stearic acid content of 85% by weight, a layer containing the same mixture having a stearic acid content of 98% by weight, and a layer containing the same mixture having a stearic acid content of 90% by weight, which layers are laminated in this order from inner layer); and the like.

The multilayered coating layer wherein the cases (A) and (B) above co-exist includes a multilayered coating layer in which the layers in the case (A) constitute the inner layers and the layers in the case (B) constitute the outer layers, a multilayered coating layer in which the layers in the case (A) constitute the outer layers and the layers in the case (B) constitute the inner layers, and a multilayered coating layer in which the layers in the cases (A) and (B) are randomly arranged.

The preparation of the present invention is able to slow the rate of a drug release by increasing the number of layers of a multilayered coating layer. Thus, the rate of the drug release can be adjusted by increasing or decreasing the number of layers.

There are two ways to increase the number of layers, namely simply adding new layers (in this case, the coating ratio of the entire multilayered coating layer (% by weight of the coating layer to the core substance) increases as the number of layers increases), and increasing the number of layers without altering the coating ratio of the entire multilayered coating layer (in this case, it is necessary to decrease the coating ratio of each layer that forms the multilayered coating layer in order to increase the number of layers). If the latter method is used, release can be efficiently controlled in cases when it is not desirable to increase the coating ratio, in order to increase a drug content of the preparation, as in the manner of drugs having extremely high water solubility and a high dosage despite it being difficult to control drug release at a low coating ratio. The method is also useful even in cases in which control of drug release is difficult at low coating ratios due to small particle size of the core substance (e.g., 200 μm or less) and large surface area per unit weight.

For example, in the case of a core substance containing acetaminophen and having a mean particle size of 150 μm being coated by a multilayered coating layer in which layers containing a stearic acid-hydroxypropyl cellulose mixture having a stearic acid content of 98 wt %, and layers containing the same mixture having a stearic acid content of 90 wt % are alternately laminated, if the number of layers of the multilayered coating layer is taken to be six and the coating ratio per layer is taken to be 10 wt % (coating ratio of the entire multilayered coating layer is 60 wt %), the T50% value in the dissolution test according to the method described in the 13$^{th}$ Edition of the Japanese Pharmacopoeia (Method 2, test fluid: water, 37° C., paddle rotating speed: 100 rpm) is about 3 hours. However, if the number of layers of the multilayered coating layer is taken to be 12 and the coating ratio per layer is taken to be 5% (coating ratio of the entire multilayered coating layer is still 60%), the T50% value under the same conditions can be made to be about 8 hours. Thus even if the coating ratio of the overall multilayered coating layer is the same, the rate of the drug release can be slowed by decreasing the coating ratio of each layer and increasing the number of layers.

In addition, although obvious, the rate of the release can also be slowed by increasing the coating ratio of the overall multilayered coating ratio as a result of increasing the coating ratio of each layer that forms the multilayered coating layer. In this case, the coating ratio of each layer may be mutually different, or the coating ratios of all layers may be the same.

Thus, for a person with ordinary skill in the art, the number of layers and coating ratio of a multilayered coating layer could be easily determined so as to obtain the desired drug release rate by considering the solubility of the drug and the physical properties and so forth of the hydrophobic organic compound and water-soluble polymer based on the above phenomenon. If one were to go so far as to indicate specific examples of the number of layers and coating ratio of the multilayered coating layer in the preparation of the present invention, the number of layers is preferably within the range of 2–200 layers and the coating ratio is preferably within the range of 3–300 wt %, while more preferably, the number of layers is in the range of 4–50 layers and the coating ratio is in the range of 10–150 wt %.

The preparation of the present invention is prepared by spray-coating a solution containing a hydrophobic organic substance-water-soluble polymer mixture onto a drug-containing core substance using a known coating apparatus, followed by spray-coating a different hydrophobic organic compound-water-soluble polymer mixture onto the resulting coating layer and repeating this process until the desired multilayered recording layer is obtained.

There are no particular restrictions on the solvent of the coating solution provided that it dissolves both the hydrophobic organic compound and water-soluble polymer, examples of which include alcohols such as methanol, ethanol, n-propanol, isopropanol, n-butanol, 2-methoxyethanol (trade name: Methyl Cellosolve, Katayama Chemical) and 2-ethoxyethanol (trade name: Cellosolve, Katayama Chemical), hydrocarbons such as hexane, cyclohexane, petroleum ether, petroleum benzene, ligroin, benzene, toluene and xylene, ketones such as acetone and methyl ethyl ketone, halogenated hydrocarbons such as dichloromethane, chloroform, carbon tetrachloride, ethylene dichloride, trichloroethylene and 1,1,1-trichloroethane, esters such as methylacetate ester, ethylacetate ester and butylacetate ester, and ethers such as isopropyl ether and dioxane.

These solvents should be selected according to the hydrophobic organic compound and water-soluble polymer used, and two or more kinds can be used by suitably blending.

Of these, particularly preferable solvents are alcohols, and among those, a particularly preferable alcohol is ethanol.

Examples of coating apparatuses include a fluidized bed coating apparatus, centrifugal fluidized bed coating apparatus and pan coating apparatus. Those apparatuses of the side spraying type or bottom spraying type are particularly preferable.

Spraying of coating solution should be performed continuously by sequentially changing the coating solution until the desired multilayered coating layer is obtained.

The core substance used in the present invention may consist of drug alone or drug and various types of additives normally used in this field. There are no particular restrictions on the form of the core substance, examples of which include fine particles, granules, tablets and capsules. Of these, fine particles, and especially those having a mean particle size of 200 µm or less, are particularly preferable.

There are no particular restrictions on the drug provided it is used for the purpose of oral administration, examples of various drugs include: (1) Antipyretics, analgesics and antiphlogistics (such as indometacin, acetylsalicylic acid, diclofenac sodium, ketoprofen, ibuprofen, mefenamic acid, azulene, phenacetin, isopropyl antipyrine, acetaminophen, benzadac, phenylbutazone, flufenamic acid, sodium salicylate, salicylamide, sazapyrine and etodolac), (2) anti-inflammatory steroids (such as dexamethasone, hydrocortisone, prednisolone and triamcinolone), (3) antiulcer drugs (such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride), (4) coronary vasodilators (such as nifedipine, isosorbide dinitrate, diltiazem hydrochloride, trapidil, dipyridamole, dilazep hydrochloride, verapamil, nicardipine, nicardipine hydrochloride and verapamil hydrochloride), (5) peripheral vasodilators (such as ifenprodil tartrate, cinepacide maleate, ciclandelate, cynnaridine and pentoxyphylin), (6) antibiotics (such as ampicillin, amoxicillin, cefalexin, erythromycinethyl succinate, vacampicillin hydrochloride, minocycline hydrochloride, chloramphenicol, tetracycline, erythromycin, ceftazidime, cefuroxime sodium, aspoxicillin and lichipenam acoxyl hydrate), (7) synthetic antimicrobials (such as nalidixic acid, piromidic acid, pipemidic acid trihydrate, enoxacin, cinoxacin, ofloxacin, norfloxacin, ciprofloxacin hydrochloride and sulfamethoxazole-trimethoprim), (8) antiviral agents (such as aciclovir and ganciclovir), (9) anticonvulsants (such as propantheline bromide, atropine sulfate, oxitropium bromide, timepidium bromide, scopolamine butylbromide, trospium chloride, butropiumbromide, N-methylscopolaminemethylsulfate and methyloctatropine bromide), (10) antitussives (such as tipepedine hibenzate, methylephedrine hydrochloride, codeine phosphate, tranilast, dextromethorphan hydrobromide, dimemorfan phosphate, clobutinol hydrochloride, fominoben hydrochloride, benproperine phosphate, eprazinone hydrochloride, clofedanol hydrochloride, ephedrine hydrochloride, noscapine, pentoxyverine citrate, oxeladin citrate and isoaminyl citrate),(11) expectorants (such as bromhexine hydrochloride, carbocysteine, ethyl cysteine hydrochloride and methylcysteine hydrochloride), (12) bronchodilators (such as theophylline, aminophylline, sodium cromoglicate, procaterol hydrochloride, trimetoquinol hydrochloride, diprophilline, salbutamol sulfate, clorprenaline hydrochloride, formoterol fumarate, ocriprenaline sulfate, pilbuterol hydrochloride, hexoprenaline sulfate, bitolterol mesilate, clenbuterol hydrochloride, terbutaline sulfate, malbuterol hydrochloride, fenoterol hydrobromide and methoxyphenamine hydrochloride), (13) cardiotonics (such as dopamine hydrochloride, dobutamine hydrochloride, docarpamine, denopamine, caffeine, digoxin, digitoxin and ubidecarenone), (14) diuretics (such as furosemide, acetazolamide, triclormethiazide, methylclothiazide, hydrochlorothiazide, hydroflumethiazide, ethiazide, cyclopenthiazide, spironolactone, triamterene, florothiazide, piretanide, mefruside, etacrynic acid, azosemide and clofenamide), (15) muscle relaxants (such as chlorphenesin carbamate, tolperisone hydrochloride, eperisone hydrochloride, tizanidine hydrochloride, mefenicine, chlorzoxazone, phenprobamate, methocarbamol, chlormezazone, pridinol mesilate, afloqualone, baclofen and dantrolene sodium), (16) cerebral metabolism ameliorants (such as nicergoline, meclofenoxate hydrochloride and taltirelin), (17) minor tranquilizers (such as oxazolam, diazepam, clotiazepam, medazepam, temazepam, fludiazepam, meprobamate, nitrazepam and chlordiazepoxide), (18) major tranquilizers (such as sulpiride, clocapramine hydrochloride, zotepine, chlorpromazine and haloperidol), (19) β-blockers (such as bisoprolol fumarate, pindolol, propranolol hydrochloride, carteolol hydrochloride, metoprolol tartrate, labetanol hydrochloride, acebutolol hydrochloride, bufetolol hydrochloride, alprenolol hydrochloride, arotinolol hydrochloride, oxprenolol hydrochloride, nadolol, bucumorol hydrochloride, indenolol hydrochloride, timolol maleate, befunolol hydrochloride and bupranolol hydrochloride), (20) antiarrthymics (such as procainamide hydrochloride, diso-pyramide, ajmaline, quinidine sulfate, aprindine hydrochloride, propafenone hydrochloride, mexiletine hydrochloride and azmilide hydrochloride), (21) athrifuges (such as allopurinol, probenicid, colchicine, sulfinpyrazone, benzbromarone and bucolome), (22) anticoagulants (such as ticlopidine hydrochloride, dicumarol, potassium warfarin, and (2R,3R)-3-acetoxy-5-[2-(dimethylamino)ethyl]-2,3-dihydro-8-methyl-2-(4-methylphenyl)-1,5-benzothiazepin-4(5H)-one-maleate), (23) thrombolytics (such as methyl (2E,3Z)-3-benzylidene-4-(3,5-dimethoxy-α-methylbenzylidene)-N-(4-methylpiperazin-1-yl)-succinamate hydrochloride), (24) liver disease drugs (such as (±)r-5-hydroxymethyl-t-7-(3,4-dimethoxyphenyl)-4-oxo-4,5,6,7-tetrahydrobenzo [b] furan-c-6-carboxylactone), (25) antiepileptics (such as phenytoin, sodium valproate, metalbital and carbamazepine), (26) antihistamines (such as chlorpheniramine maleate, clemastine fumarate, mequitazine, alimemazine tartrate, cyproheptadine hydrochloride and bepotastin besilate), (27) antiemitics (such as difenidol hydrochloride, metoclopramide, domperidone and betahistine mesilate and trimebutine maleate), (28) depressors (such as dimethylaminoethyl reserpilinate dihydrochloride, rescinnamine, methyldopa, prazocin hydrochloride, bunazosin hydrochloride, clonidine hydrochloride, budralazine, urapidil and N-[6-[2-[(5-bromo-2-pyrimidinyl)oxy]ethoxy]-5-(4-methylphenyl)-4-pyrimidinyl]-4-(2-hydroxy-1,1-dimethyl-ethyl)benzenesulfonamide sodium), (29) hyperlipidemia agents (such as pravastatin sodium and fluvastatin sodium), (30) sympathetic nervous stimulants (such as dihydroergotamine mesilate and isoproterenol hydrochloride, etilefrine hydrochloride), (31) oral diabetes therapeutic drugs (such as glibenclamide, tolbutamide and glimidine sodium), (32) oral carcinostatics (such as malimastat), (33) alkaloid narcotics (such as morphine, codeine and cocaine), (34) vitamins (such as vitamin B1, vitamin B2, vitamin B6, vitamin B12, vitamin C and folic acid), (35) thamuria therapeutic drugs (such as flavoxate hydrochloride, oxybutynin hydrochloride and terolidine hydrochloride), and, (36) angiotensin converting enzyme inhibitors (such as imidapril hydrochloride, enalapril maleate, alacepril and delapril hydrochloride).

There are no particular restrictions on the drug additives, and all those that can be used in the form of solid preparations can be suitably used. Examples of such additives include excipients such as lactose, sucrose, mannitol, xylitol, erythritol, sorbitol, maltitol, calcium citrate, calcium phosphate, crystalline cellulose and magnesium aluminate metasilicate, disintegrating agents such as cornstarch, potato starch, sodium carboxymethyl starch, partially pregelatinized starch, calcium carboxymethyl cellulose, carboxymethyl cellulose, low-substituted hydroxypropyl cellulose, sodium crosslinked carboxymethyl cellulose and crosslinked polyvinyl pyrrolidone, binders such as hydroxypropyl cellulose, hydroxypropylmethyl cellulose, polyvinyl pyrrolidone, polyethylene glycol, dextrin and pregelatinized starch, lubricants such as magnesium stearate, calcium stearate, talc, light anhydrous silicic acid and hydrated silicon dioxide, surfactants such as phospholipid, glycerin fatty acid ester, sorbitan fatty acid ester, polyoxyethylene fatty acid ester, polyethylene glycol fatty acid ester, polyoxyethylene hydrogenated castor oil, polyoxyethylene alkyl ether and sucrose fatty acid ester, or fragrances such as orange and strawberry, colorants such as iron sesquioxide, yellow iron sesquioxide, yellow food dye no. 5, yellow food dye no. 4 and aluminum lake, sweeteners such as saccharine and aspartame, and correctives such as citric acid, sodium citrate, succinic acid, tartaric acid, fumaric acid and glutamic acid, and solubilizer such as cyclodextrin, arginine, lysine and tris-aminomethane.

In the case of using fine particles or granules for the core substance, these can be prepared by known granulation methods such as wet granulation, dry granulation, layering granulation and impregnating granulation.

When preparing by wet granulation, after mixing drug and various preparation additives in accordance with routine methods, binder solution is added followed by granulation with a agitating granulating machine or high-speed agitating granulating machine, or after mixing and kneading binder solution into a mixture of drug and various preparation additives, granulation and grading should be performed using an extrusion granulating machine. In addition, granulation may also be performed by spraying the mixture of drug and various preparation additives with a binder solution while flowing using a fluidized bed granulating machine or a centrifugal fluidized bed granulating machine and so forth.

When preparing by dry granulation, a mixture of drug and various preparation additives should be granulated using a roller compacter and roll granulator, etc.

In the case of preparing by layering granulation, drug (along with various preparation additives as necessary) should be added while spraying a binder solution onto a rolling inert carrier using a centrifugal fluidizing granulating machine and so forth so that the drug is adhered to the carrier. At this time, a substance such as oil or wax that is melted by heating (heat-melting substance) may be added while heating along with drug in place of the binder solution and melted to allow drug to adhere to the carrier.

Examples of inert carriers include crystals or sugars or inorganic salts such as crystal lactose, crystalline cellulose and crystal sodium chloride, and spherical granulation products (such as the spherical granulation product of crystalline cellulose (trade name: Avicel SP, Asahi Chemical Industry), the spherical granulation product of crystalline cellulose and lactose (trade name: Nonpareil NP-5 and NP-7, Freund Industry), the spherical granulation product of refined sucrose (trade name: Nonpareil-103, Freund Industry) and the spherical granulation product of lactose and alpha-converted starch).

When preparing by impregnating granulation, a suitable concentration of drug solution is mixed with a porous carrier, and after adequately retaining the drug solution inside the pores of the carrier, the impregnated carrier should be dried and the solvent removed.

Examples of porous carriers include magnesium aluminometasilicate (trade name: Neusilin, Fuji Chemical Industries) and calcium silicate (trade name: FLORITE, Eisai).

In the case of using tablets for the core substance, a mixture of drug and various preparation additives is mixed followed directly by compression to form into tablets, or after obtaining granules according to the methods described above, disintegrating agent, lubricant and so forth are added followed by compression to form into tablets.

In addition, in the case of using capsules for the core substance, a hard capsule or soft capsule filled with drug should be used as it is.

Moreover, in the preparation of the present invention, at least one layer of water-soluble polymer, water-insoluble polymer, enteric polymer, gastrosoluble polymer or a mixture thereof (with the undercoating layer on the inside and the overcoating layer on the outside) can be provided on the inside or outside of the multilayered coating layer for various purposes such as preventing interaction between drug and multilayered coating layer components, adjusting the rate of the release more efficiently, enhancing resistance to stomach acidity or enhancing preparation strength.

Examples of water-soluble polymers include the above water-soluble polymers used in the multilayered coating layer. Examples of water-insoluble polymers include water-insoluble cellulose ethers such as ethyl cellulose, and water-insoluble acrylic copolymers such as ethyl acrylate methyl•methacrylate•methacrylic acid trimethyl chloride ammonium ethyl copolymer (e.g., trade name: Eudragit RS, Röhm Pharma), and methyl methacrylate•ethyl acrylate copolymer (e.g., trade name: Eudragit NE30D, Röhm Pharma). Examples of enteric polymers include enteric cellulose derivatives such as hydroxypropylmethyl cellulose acetate succinate, hydroxypropylmethyl cellulose phthalate, hydroxymethylethyl cellulose phthalate, cellulose acetate phthalate, cellulose acetate succinate, cellulose acetate maleate, cellulose benzoate phthalate, cellulose propionate phthalate, methyl cellulose phthalate, carboxymethyl ethyl cellulose and ethyl hydroxyethyl cellulose phthalate, enteric acrylic copolymers such as styrene•acrylic acid copolymer, methyl acrylate•acrylic acid copolymer, methyl acrylate•methacrylic acid copolymer, butyl acrylate•styrene•acrylic acid copolymer, methacrylic acid•methyl methacrylate copolymer (e.g., trade name: Eudragit L100, Eudragit S, Röhm Pharma), methacrylic acid•ethyl acrylate copolymer (e.g., trade name: Eudragit L100-55, Röhm Pharma) and methyl acrylate•methacrylic acid•octyl acrylate copolymer, enteric maleic acid copolymers such as styrene•maleic anhydride copolymer, styrene•maleic monoester copolymer, vinyl methyl ether•maleic anhydride copolymer, ethylene•maleic anhydride copolymer, vinyl butyl ether•maleic anhydride copolymer, acrylonitrile•methyl acrylate•maleic anhydride copolymer, and butyl acrylate•styrene•maleic anhydride copolymer, and enteric polyvinyl derivatives such as polyvinyl alcohol phthalate, polyvinyl acetal phthalate, polyvinyl butyrate phthalate and polyvinyl acetacetal phthalate. Examples of gastrosoluble polymers include gastrosoluble polyvinyl derivatives such as polyvinyl acetal diethylaminoacetate, and gastrosoluble acrylic copolymers such as methyl methacrylate•butyl methacrylate•dimethylaminoethyl methacrylate copolymer (e.g., trade name: Eudragit E, Röhm Pharma).

Undercoating and overcoating should be performed in accordance with known coating methods, and solutions or dispersions of the above components should be spray-coated onto the core substance for the undercoating, or spray-coated onto the multilayered coating layer for the overcoating using a known coating apparatus.

It is particularly preferable to provide an undercoating layer for enhancing preparation strength on the inside of the multilayered coating layer. Said undercoating layer preferably has for its main component the above water-insoluble polymer substance and so forth, with ethyl cellulose being particularly preferable. The coating ratio of the undercoating layer for enhancing preparation strength is preferably 1–150 wt %, and particularly preferably 5–50 wt %.

Although the preparation of the present invention obtained in this manner can be used as is in the form of an orally administered preparation, in the case of using fine particles or granules for the core substance, various additives may be added as necessary to the resulting multilayered coating granules (or fine particles) followed by compression to form tablets, filled into capsules to form capsule preparations, or formed into a drug form suitable for various forms of oral administration.

EXAMPLES

Hereinbelow, the present invention will be described in more detail with reference to the following Comparative Examples and Examples, which should not be construed as limiting the scope of the present invention.

Comparative Example 1

100 g of acetaminophen and 40 g of hydroxypropyl cellulose (HPC-SL; manufactured by NIPPON SODA CO., LTD.) were dissolved in 500 g of ethanol, and the resultant solution and 100 g of magnesium aluminomethasilicate (Neusilin NS2N; manufactured by Fuji Chemical Industry Co., Ltd.) were mixed with each other and stirred using a Shinagawa-type versatile mixer, to thereby perform an impregnating granulation. After drying, the resultant granules were subjected to sieving, to obtain fine particles having a particle diameter of 75 to 180 μm (average particle diameter: 150 μm), and the obtained fine particles were used as a core substance.

Using a Wurster-type fluidized bed coating machine (GPCG-1; manufactured by Glatt Co.), an ethanol solution of a stearic acid-hydroxypropyl cellulose mixture having a stearic acid content of 98% by weight {stearic acid (manufactured by Kao Corporation): 4.9% by weight; hydroxypropyl cellulose: 0.1% by weight; ethanol: 95% by weight} was applied to 100 g of the core substance in a fluid state by spray-coating, to thereby obtain fine particles coated with a stearic acid-hydroxypropyl cellulose mixture having a stearic acid content of 98% by weight. The coating ratios (% by weight of the coating layer relative to the core substance) were 40, 60, and 80% by weight.

With respect to the coated fine particles obtained, a dissolution test was conducted according to the method described in the 13$^{th}$ revision of the Japanese Pharmacopoeia (Method 2, test liquid:water, 37° C.; paddle rotating speed: 100 rpm). The dissolution behavior was examined, and the results were shown in FIG. 1.

Figure 1:
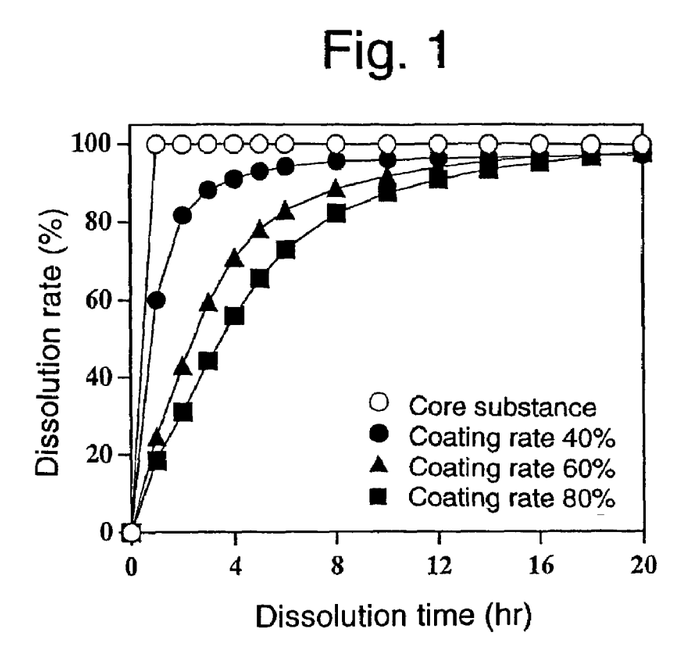
FIG. 1 is a graph showing the dissolution behavior of the fine particles coated with a stearic acid-hydroxypropyl cellulose mixture having a stearic acid content of 98% by weight.

As is apparent from FIG. 1, in accordance with the increase in the coating ratio, the releasing rate was suppressed; however, even in the particles having a coating ratio of 80% by weight, the T50% (the time required for a half amount of the acetaminophen contained in the preparation is dissolved) was as short as 3.5 hours. Thus, the particles coated with a single layer of the stearic acid-hydroxypropyl cellulose mixture having a stearic acid content of 98% by weight exhibited an effect of suppressing the release to some extent, but it was impossible to effectively suppress the drug release with a small coating amount.

However, as is apparent from the D20h (a dissolution ratio after 20 hours) values, in the fine particles coated with the stearic acid-hydroxypropyl cellulose mixture having a stearic acid content of 98% by weight, almost no phenomenon of reaching the upper limit of drug release was recognized, and also in the fine particles having a coating ratio of 80% by weight, the D20h was about 100%.

Comparative Example 2

Using a Wurster-type fluidized bed coating machine (GPCG-1; manufactured by Glatt Co.), an ethanol solution of a stearic acid-hydroxypropyl cellulose mixture having a stearic acid content of 90% by weight (stearic acid: 4.5% by weight; hydroxypropyl cellulose: 0.5% by weight; ethanol: 95% by weight) was applied to 100 g of the core substance obtained in Comparative Example 1 in a fluid state by spray-coating, to thereby obtain fine particles coated with a stearic acid-hydroxypropyl cellulose mixture having a stearic acid content of 90% by weight. The coating ratios were 40, 60, and 80% by weight.

Figure 2:
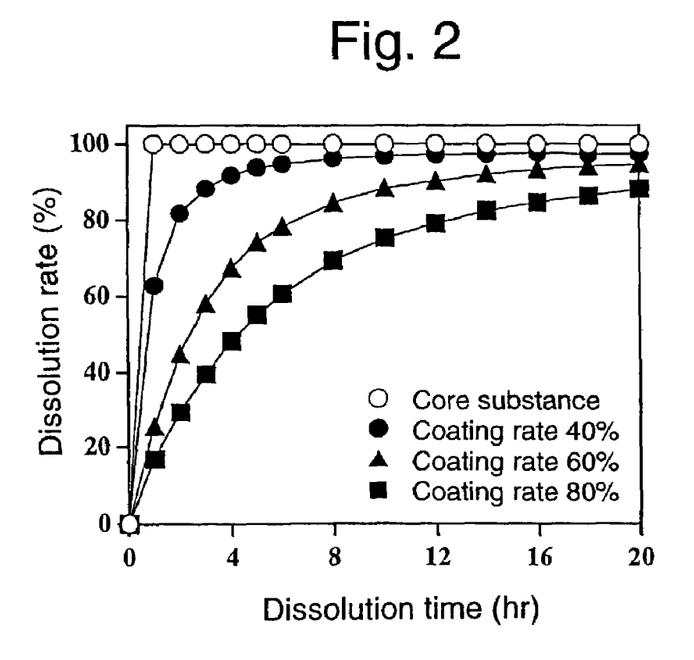
FIG. 2 is a graph showing the dissolution behavior of the fine particles coated with a stearic acid-hydroxypropyl cellulose mixture having a stearic acid content of 90% by weight.

With respect to the coated fine particles obtained, a dissolution test was conducted in the same manner as in Comparative Example 1, and the dissolution behavior in the test liquid was examined, and the results were shown in FIG. 2.

As is apparent from FIG. 2, in accordance with the increase in the coating ratio, the releasing rate was suppressed; however, even in the particles having a coating ratio of 80% by weight, the T50% was as short as 4.2 hours. Thus, the particles coated with a single layer of the stearic acid-hydroxypropyl cellulose mixture having a stearic acid content of 90% by weight exhibited an effect of suppressing the release to some extent, but it was impossible to effectively suppress the drug release with a small coating amount.

However, as is apparent from the D20h, in the fine particles coated with the stearic acid-hydroxypropyl cellulose mixture having a stearic acid content of 90% by weight, almost no phenomenon of reaching the upper limit of drug release was recognized, and also in the fine particles having a coating ratio of 80% by weight, the D20h was about 90%.

Example 1

Using a Wurster-type fluidized bed coating machine (GPCG-1; manufactured by Glatt Co.), an ethanol solution of the stearic acid-hydroxypropyl cellulose mixture having a stearic acid content of 98% by weight used in Comparative Example 1 and an ethanol solution of the stearic acid-hydroxypropyl cellulose mixture having a stearic acid content of 90% by weight used in Comparative Example 2 were alternately applied in this order to 100 g of the core substance obtained in Comparative Example 1 in a fluid state by spray-coating, to thereby obtain multilayer-coated fine particles which were alternately laminated with a layer of the stearic acid-hydroxypropyl cellulose mixture having a stearic acid content of 98% by weight and a layer of the stearic acid-hydroxypropyl cellulose mixture having a stearic acid content of 90% by weight. The coating ratio of each layer was 10% by weight, and the coating ratios of the multilayered coating layers were 40% by weight (4 layers), 60% by weight (6 layers), and 80% by weight (8 layers).

Figure 3:
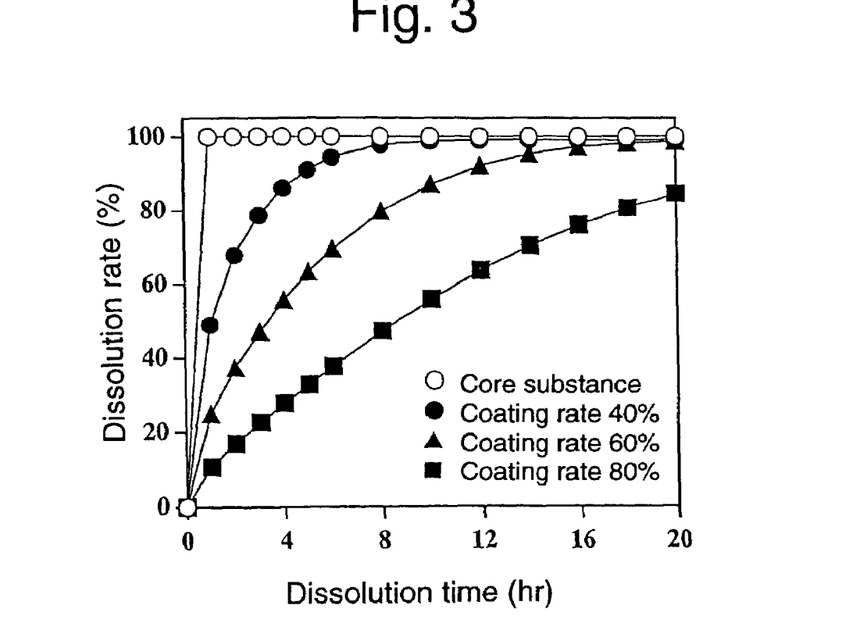
FIG. 3 is a graph showing the dissolution behavior of the multilayer-coated fine particles which are alternately coated with a layer of a stearic acid-hydroxypropyl cellulose mixture having a stearic acid content of 98% by weight and a layer of a stearic acid-hydroxypropyl cellulose mixture having a stearic acid content of 90% by weight (coating ratio of each layer: 10% by weight).

With respect to the multilayer-coated fine particles obtained, a dissolution test was conducted in the same manner as in Comparative Example 1, and the dissolution behavior in the test liquid was examined, and the results were shown in FIG. 3.

As is apparent from FIG. 3, in accordance with the increase in the number of the multilayered coating layers, the release of the drug was suppressed.

In addition, when a comparison is made between the fine particles having the same coating ratio, the multilayer-coated fine particles obtained in Example 1 exhibited a drug releasing rate which was remarkably lower than those of the fine particles obtained in Comparative Examples 1 and 2 (the T50% of the fine particles having a coating ratio of 80% by weight was 8.6 hours). Therefore, it has been found that the fine particles which are alternately coated with mixtures having different stearic acid contents can effectively suppress the drug release, as compared to the fine particles coated with a mixture with a fixed stearic acid content.

Further, the D20h of the multilayer-coated fine particles having coating ratios of up to 60% by weight obtained in Example 1 was approximately 100%, and that of the fine particles having a coating ratio of 80% by weight was 85%, and thus, almost no phenomenon of reaching the upper limit of drug release was recognized.

Example 2

Using a Wurster-type fluidized bed coating machine (GPCG-1; manufactured by Glatt Co.), an ethanol solution of the stearic acid-hydroxypropyl cellulose mixture having a stearic acid content of 98% by weight used in Comparative Example 1 and an ethanol solution of the stearic acid-hydroxypropyl cellulose mixture having a stearic acid content of 90% by weight used in Comparative Example 2 were alternately applied in this order to 100 g of the core substance obtained in Comparative Example 1 in a fluid state by spray-coating, to thereby obtain multilayer-coated fine particles which were alternately coated with a layer of the stearic acid-hydroxypropyl cellulose mixture having a stearic acid content of 98% by weight and a layer of the stearic acid-hydroxypropyl cellulose mixture having a stearic acid content of 90% by weight. The coating ratio of each layer was 5% by weight, and the coating ratios of the multilayered coating layers were 40% by weight (8 layers), 50% by weight (10 layers), and 60% by weight (12 layers).

Figure 4:
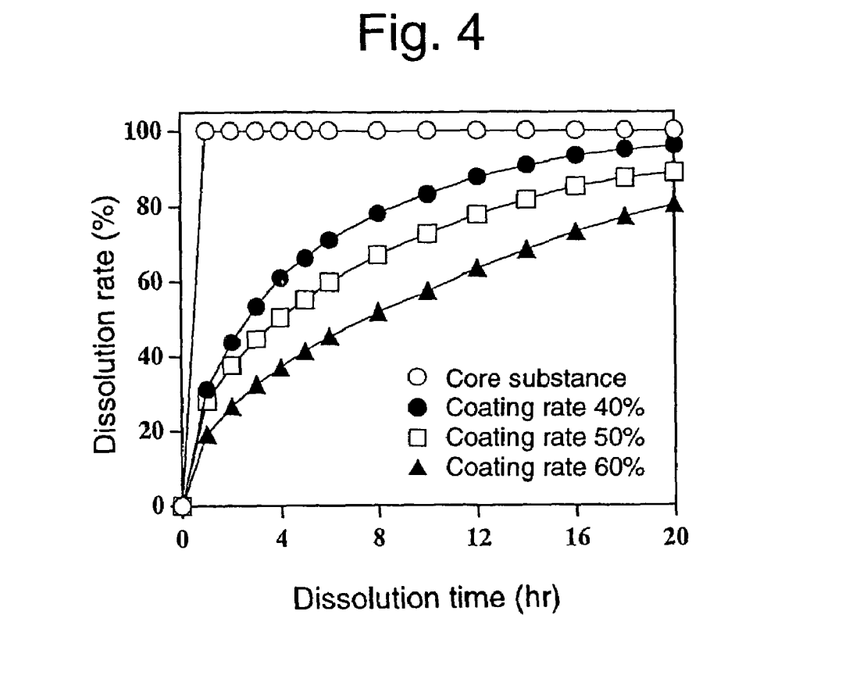
FIG. 4 is a graph showing the dissolution behavior of the multilayer-coated fine particles which are alternately coated with a layer of a stearic acid-hydroxypropyl cellulose mixture having a stearic acid content of 98% by weight and a layer of a stearic acid-hydroxypropyl cellulose mixture having a stearic acid content of 90% by weight (coating ratio of each layer: 5% by weight).

With respect to the multilayer-coated fine particles obtained, a dissolution test was conducted in the same manner as in Comparative Example 1, and the dissolution behavior in the test liquid was examined, and the results were shown in FIG. 4.

When a comparison is made between the multilayer-coated fine particles obtained in Example 1 and the multilayer-coated fine particles obtained in Example 2, both having the same coating ratio, the multilayer-coated fine particles obtained in Example 2 exhibited a lower releasing rate. Therefore, it has been found that, in the fine particles coated with a multilayered coating layer having the same coating ratio, the larger the number of the layers, the higher the effect of suppressing the drug release.

Example 3

Using a Wurster-type fluidized bed coating machine (GPCG-1; manufactured by Glatt Co.), an ethanol solution of the stearic acid-hydroxypropyl cellulose mixture having a stearic acid content of 90% by weight used in Comparative Example 2 and an ethanol solution of the stearic acid-hydroxypropyl cellulose mixture having a stearic acid content of 98% by weight used in Comparative Example 1 were alternately applied in this order to 100 g of the core substance obtained in Comparative Example 1 in a fluid state by spray-coating, to thereby obtain multilayer-coated fine particles which were alternately coated with a layer of the stearic acid-hydroxypropyl cellulose mixture having a stearic acid content of 90% by weight and a layer of the stearic acid-hydroxypropyl cellulose mixture having a stearic acid content of 98% by weight. The coating ratio of each layer was 10% by weight, and the coating ratios of the multilayered coating layers were 40% by weight (4 layers), 50% by weight (5 layers), and 60% by weight (6 layers).

Figure 5:
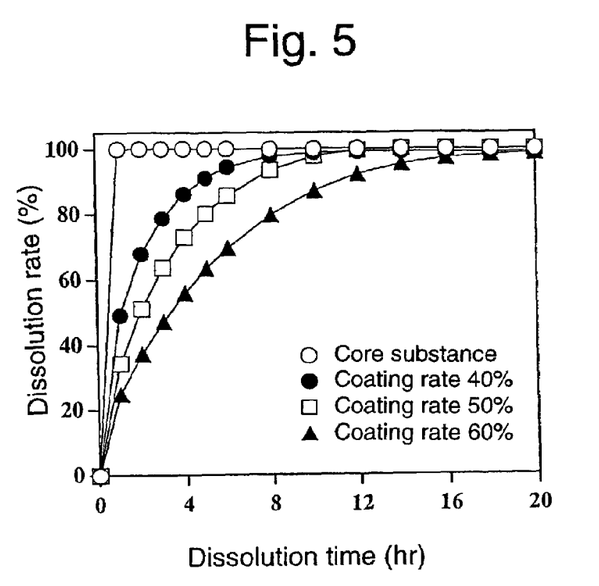
FIG. 5 is a graph showing the dissolution behavior of the multilayer-coated fine particles which are alternately coated with a layer of a stearic acid-hydroxypropyl cellulose mixture having a stearic acid content of 90% by weight and a layer of a stearic acid-hydroxypropyl cellulose mixture having a stearic acid content of 98% by weight (coating ratio of each layer: 10% by weight).

With respect to the multilayer-coated fine particles obtained, a dissolution test was conducted in the same manner as in Comparative Example 1, and the dissolution behavior in the test liquid was examined, and the results were shown in FIG. 5.

When a comparison is made between the multilayer-coated fine particles obtained in Example 1 and the multilayer-coated fine particles obtained in Example 3, both having the same coating ratio, there was no difference therebetween in the releasing rate. Therefore, it has been found that there is no difference in the effect of suppressing the drug release between the fine particles which are alternately coated with the two mixtures having different stearic acid contents, except that the coating order of the two mixtures is reversed.

Example 4

Using a Wurster-type fluidized bed coating machine (GPCG-1; manufactured by Glatt Co.), an ethanol solution of a stearic acid-hydroxypropyl cellulose mixture having a stearic acid content of 85% by weight (stearic acid: 4.25% by weight; hydroxypropyl cellulose: 0.75% by weight; ethanol: 95% by weight) and an ethanol solution of the stearic acid-hydroxypropyl cellulose mixture having a stearic acid content of 98% by weight used in Comparative Example 1 were alternately applied in this order to 100 g of the core substance obtained in Comparative Example 1 in a fluid state by spray-coating, to thereby obtain multilayer-coated fine particles which were alternately coated with a layer of the stearic acid-hydroxypropyl cellulose mixture having a stearic acid content of 85% by weight and a layer of the stearic acid-hydroxypropyl cellulose mixture having a stearic acid content of 98% by weight. The coating ratio of each layer was 10% by weight, and the coating ratios of the multilayered coating layers were 40% by weight (4 layers), 50% by weight (5 layers), and 60% by weight (6 layers).

Figure 6:
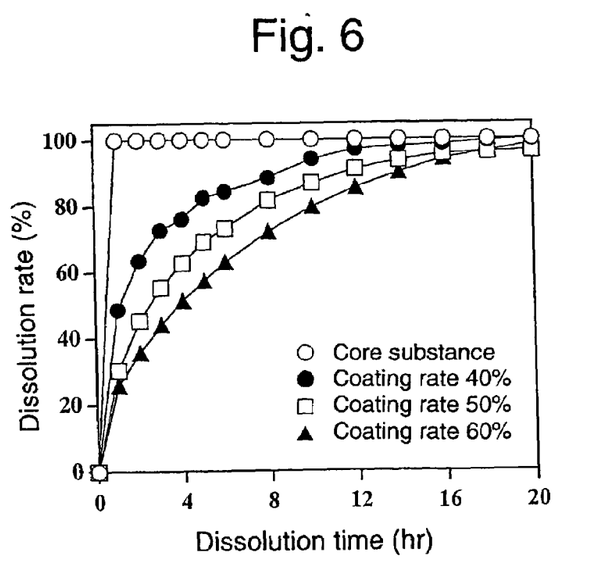
FIG. 6 is a graph showing the dissolution behavior of the multilayer-coated fine particles which are alternately coated with a layer of a stearic acid-hydroxypropyl cellulose mixture having a stearic acid content of 85% by weight and a layer of a stearic acid-hydroxypropyl cellulose mixture having a stearic acid content of 98% by weight (coating ratio of each layer: 10% by weight).

With respect to the multilayer-coated fine particles obtained, a dissolution test was conducted in the same manner as in Comparative Example 1, and the dissolution behavior in the test liquid was examined, and the results were shown in FIG. 6.

When a comparison is made between the multilayer-coated fine particles obtained in Example 3 and the multilayer-coated fine particles obtained in Example 4, both having the same coating ratio, the multilayer-coated fine particles obtained in Example 4 exhibited a lower releasing rate. Therefore, it has been found that the larger the difference in stearic acid contents between the adjacent layers in the multilayered coating layer (multilayer-coated fine particles in Example 3:8% by weight; multilayer-coated fine particles in Example 4:13% by weight), the higher the effect of suppressing the drug release.

Example 5

Using a Wurster-type fluidized bed coating machine (GPCG-1; manufactured by Glatt Co.), an ethanol solution of a palmitic acid-hydroxypropyl cellulose mixture having a palmitic acid content of 90% by weight {palmitic acid (manufactured by KATAYAMA CHEMICAL, INC.): 4.5% by weight; hydroxypropyl cellulose: 0.5% by weight; ethanol: 95% by weight} and an ethanol solution of a palmitic acid-hydroxypropyl cellulose mixture having a palmitic acid content of 98% by weight (palmitic acid: 4.9% by weight; hydroxypropyl cellulose: 0.1% by weight; ethanol: 95% by weight) were alternately applied in this order to 100 g of the core substance obtained in Comparative Example 1 in a fluid state by spray-coating, to thereby obtain multilayer-coated fine particles which were alternately coated with a layer of the palmitic acid-hydroxypropyl cellulose mixture having a palmitic acid content of 90% by weight and a layer of the palmitic acid-hydroxypropyl cellulose mixture having a palmitic acid content of 98% by weight. The coating ratio of each layer was 10% by weight, and the coating ratios of the multilayered coating layers were 120% by weight (12 layers), and 160% by weight (16 layers).

Figure 7:
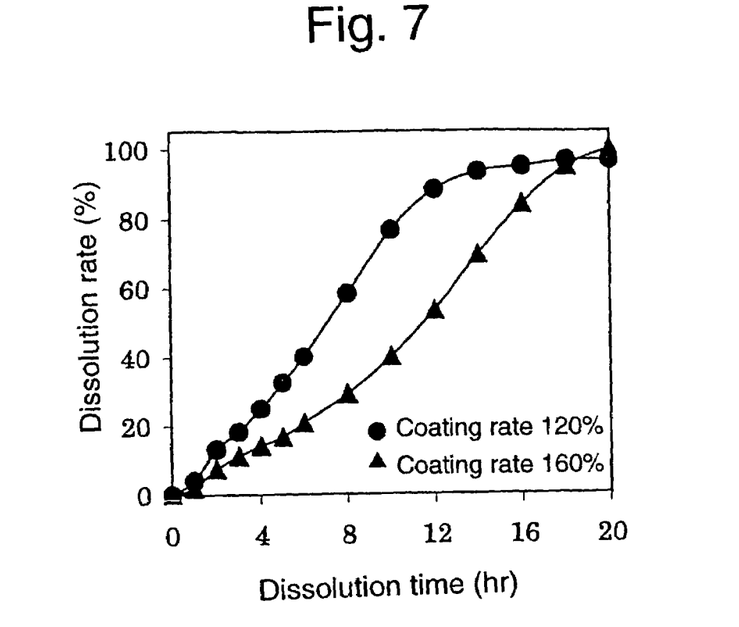
FIG. 7 is a graph showing the dissolution behavior of the multilayer-coated fine particles which are alternately coated with a layer of a palmitic acid-hydroxypropyl cellulose mixture having a palmitic acid content of 90% by weight and a layer of a palmitic acid-hydroxypropyl cellulose mixture having a palmitic acid content of 98% by weight (coating ratio of each layer: 10% by weight)

With respect to the multilayer-coated fine particles obtained, a dissolution test was conducted in the same manner as in Comparative Example 1, and the dissolution behavior in the test liquid was examined, and the results were shown in FIG. 7.

Example 6

Using a Wurster-type fluidized bed coating machine (GPCG-1; manufactured by Glatt Co.), an ethanol solution of the palmitic acid-hydroxypropyl cellulose mixture having a palmitic acid content of 90% by weight used in Example 5 and an ethanol solution of the stearic acid-hydroxypropyl cellulose mixture having a stearic acid content of 98% by weight used in Comparative Example 1 were alternately applied in this order to 100 g of the core substance obtained in Comparative Example 1 in a fluid state by spray-coating, to thereby obtain multilayer-coated fine particles which were alternately coated with a layer of the palmitic acid-hydroxypropyl cellulose mixture having a palmitic acid content of 90% by weight and a layer of the stearic acid-hydroxypropyl cellulose mixture having a stearic acid content of 98% by weight. The coating ratio of each layer was 10% by weight, and the coating ratios of the multilayered coating layers were 60% by weight (6 layers), and 80% by weight (8 layers).

Figure 8:
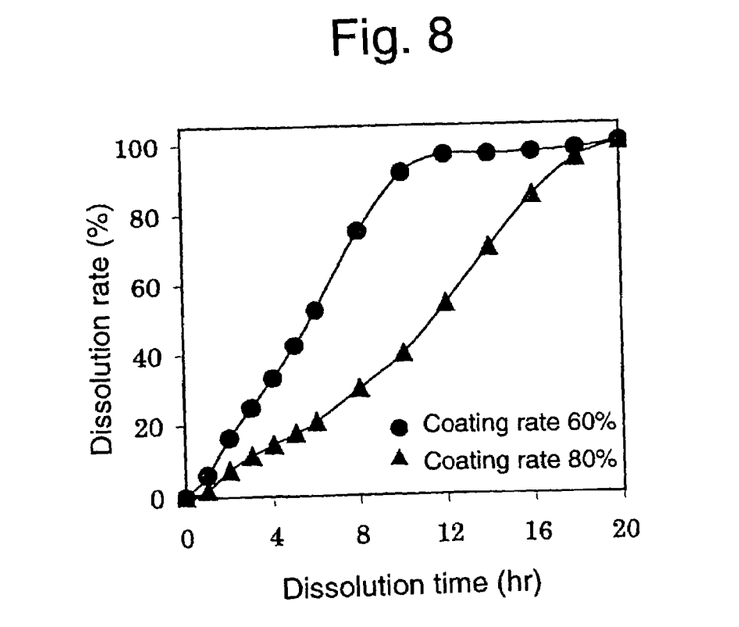
FIG. 8 is a graph showing the dissolution behavior of the multilayer-coated fine particles which are alternately coated with a layer of a palmitic acid-hydroxypropyl cellulose mixture having a palmitic acid content of 90% by weight and a layer of a stearic acid-hydroxypropyl cellulose mixture having a stearic acid content of 98% by weight (coating ratio of each layer: 10% by weight).

With respect to the multilayer-coated fine particles obtained, a dissolution test was conducted in the same manner as in Comparative Example 1, and the dissolution behavior in the test liquid was examined, and the results were shown in FIG. 8.

Example 7

Using a Wurster-type fluidized bed coating machine (GPCG-1; manufactured by Glatt Co.), an ethanol solution of a stearic acid-polyethylene glycol mixture having a stearic acid content of 90% by weight {stearic acid: 4.5% by weight; polyethylene glycol (molecular weight:about 6,000): 0.5% by weight; ethanol: 95% by weight} and an ethanol solution of a stearic acid-polyethylene glycol mixture having a stearic acid content of 98% by weight (stearic acid: 4.9% by weight; polyethylene glycol: 0.1% by weight; ethanol: 95% by weight) were alternately applied in this order to 100 g of the core substance obtained in Comparative Example 1 in a fluid state by spray-coating, to thereby obtain multilayer-coated fine particles which were alternately coated with a layer of the stearic acid-polyethylene glycol mixture having a stearic acid content of 90% by weight and a layer of the stearic acid-polyethylene glycol mixture having a stearic acid content of 98% by weight. The coating ratio of each layer was 10% by weight, and the coating ratio of the multilayered coating layer was 100% by weight (10 layers).

Figure 9:
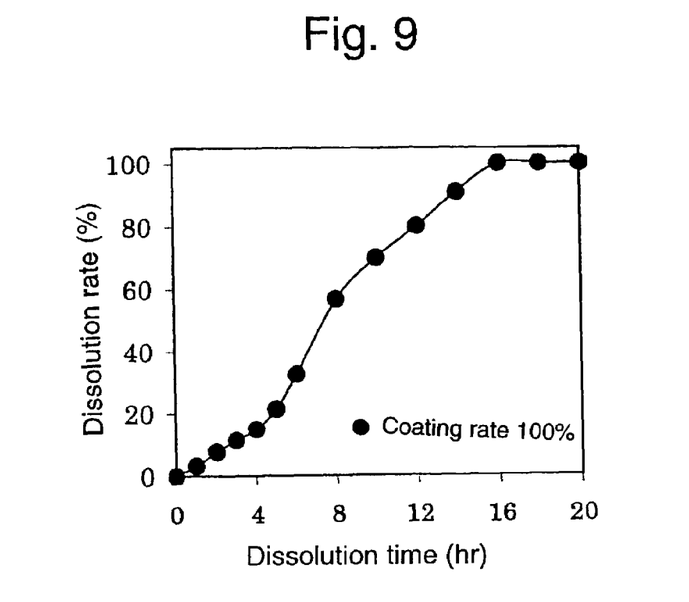
FIG. 9 is a graph showing the dissolution behavior of the multilayer-coated fine particles which are alternately coated with a layer of a stearic acid-polyethylene glycol mixture having a stearic acid content of 90% by weight and a layer of a stearic acid-polyethylene glycol mixture having a stearic acid content of 98% by weight (coating ratio of each layer: 10% by weight).

With respect to the multilayer-coated fine particles obtained, a dissolution test was conducted in the same manner as in Comparative Example 1, and the dissolution behavior in the test liquid was examined, and the results were shown in FIG. 9.

Example 8

The same procedure as in Comparative Example 1 was conducted, to thereby obtain an acetaminophen-containing core substance having a particle diameter of 75 to 180 μm (average particle diameter: 150 μm).

Using a Wurster-type fluidized bed coating machine (GPCG-1; manufactured by Glatt Co.), an ethyl cellulose solution {ETHOCEL #10 (manufactured by Shin-Etsu Chemical Co., Ltd.): 4.75% by weight; hydroxypropyl cellulose: 0.25% by weight; ethanol: 57% by weight; water: 38% by weight} was applied to 100 g of the core substance in a fluid state by spray-coating, to thereby form an undercoating layer on the core substance in a coating ratio of 30% by weight.

Then, an ethanol solution of the stearic acid-hydroxypropyl cellulose mixture having a stearic acid content of 98% by weight used in Comparative Example 1 and an ethanol solution of the stearic acid-hydroxypropyl cellulose mixture having a stearic acid content of 90% by weight used in Comparative Example 2 were alternately applied in this order to the resultant core substance by spray-coating, to thereby obtain multilayer-coated fine particles which were alternately coated with a layer of the stearic acid-hydroxypropyl cellulose mixture having a stearic acid content of 98% by weight and a layer of the stearic acid-hydroxypropyl cellulose mixture having a stearic acid content of 90% by weight. The coating ratio of each layer was 10% by weight, and the coating ratio of the multilayered coating layer was 110% by weight (11 layers).

The obtained multilayer-coated fine particles in an amount (377 mg) equivalent to 50 mg of acetaminophen were mixed with low-substitution degree hydroxypropyl cellulose in an equivalent amount, and then a No. 0-size gelatin hard capsule (manufactured by Warner-Lambert Company) was filled with the resultant mixture, to thereby obtain a capsule preparation filled with multilayer-coated fine particles.

Example 9

Using a centrifugal fluidized bed coating machine (CF-360; manufactured by FREUND INDUSTRIAL CO. LTD.), while spraying a sucrose solution (refined sugar: 20% by weight; ethanol: 40% by weight; water: 40% by weight), a mixture of 600 g of acetaminophen and 660 g of D-mannitol was added to 180 g of Nonpareil (manufactured by FREUND INDUSTRIAL CO. LTD.), to thereby effect layering granulation. After drying, the resultant granules were subjected to sieving, to thereby obtain granules having a particle diameter of 1,000 to 1,700 μm (average particle diameter: 1,200 μm), and the obtained granules were used as a core substance.

Using a centrifugal fluidized bed coating machine, an ethyl cellulose solution {ETHOCEL #10 (manufactured by Shin-Etsu Chemical Co., Ltd.): 3.5% by weight; hydroxypropyl cellulose: 1.5% by weight; ethanol: 61.75% by weight; water: 33.25% by weight} was applied to 400 g of the core substance by spray-coating, to thereby form an undercoating layer on the core substance in a coating ratio of 10% by weight.

Then, an ethanol solution of a stearic acid-hydroxypropyl cellulose mixture having a stearic acid content of 70% by weight (stearic acid: 3.15% by weight; hydroxypropyl cellulose: 1.35% by weight; ethanol: 95.5% by weight) and an ethanol solution of a stearic acid-hydroxypropyl cellulose mixture having a stearic acid content of 50% by weight (stearic acid: 2.25% by weight; hydroxypropyl cellulose: 2.25% by weight; ethanol: 95.5% by weight) were alternately applied in this order to the resultant core substance by spray-coating, to thereby obtain multilayer-coated granules which were alternately coated with a layer of the stearic acid-hydroxypropyl cellulose mixture having a stearic acid content of 70% by weight and a layer of the stearic acid-hydroxypropyl cellulose mixture having a stearic acid content of 50% by weight. The coating ratio of each layer was 2.5% by weight, and the coating ratio of the multilayered coating layer was 22.5% by weight (9 layers).

The obtained multilayer-coated granules in an amount (178 mg) equivalent to 50 mg of acetaminophen were mixed with low substituted hydroxypropyl cellulose in an equivalent amount, and then a No. 0-size gelatin hard capsule was filled with the resultant mixture, to thereby obtain a capsule preparation filled with multilayer-coated granules.

Comparative Example 3

Using a centrifugal fluidized bed coating machine, an ethyl cellulose solution {ETHOCEL #10 (manufactured by Shin-Etsu Chemical Co., Ltd.): 7% by weight; ethanol: 61.75% by weight; water: 33.25% by weight} was applied to 450 g of the core substance obtained in Example 9 by spray-coating, to thereby obtain ethyl cellulose-coated granules having a coating ratio of 4.5% by weight.

The obtained ethyl cellulose-coated granules in an amount (128 mg) equivalent to 50 mg of acetaminophen were mixed with low substituted degree hydroxypropyl cellulose in an equivalent amount, and then a No. 0-size gelatin hard capsule was filled with the resultant mixture, to thereby obtain a capsule preparation filled with ethyl cellulose-coated granules.

Experimental Example 1

Figure 10:
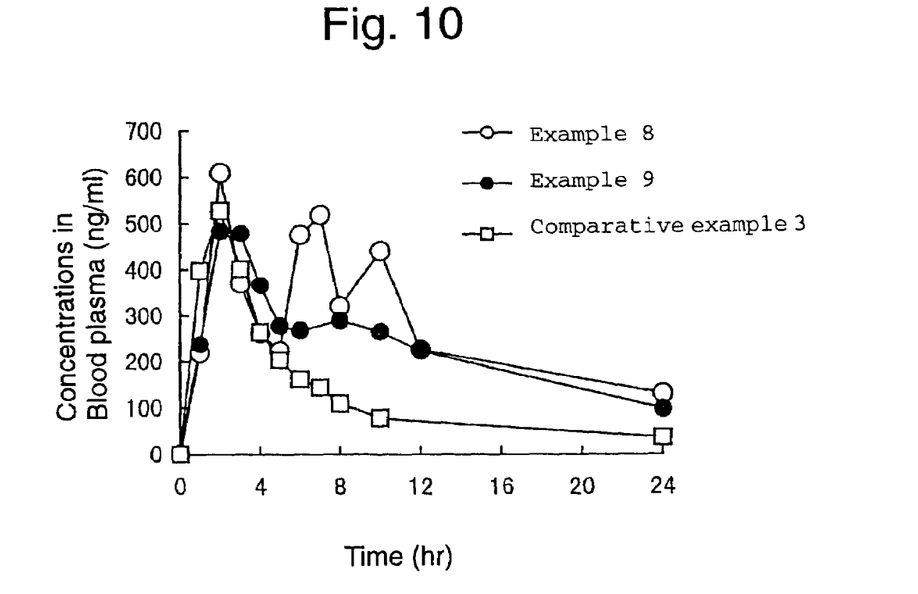
FIG. 10 is a graph showing the change of the acetaminophen concentration in blood plasma when a capsule filled with a multilayer-coated preparation and a capsule filled with an ethyl cellulose-coated preparation are administered to beagle, respectively.

Two capsule preparations (100 mg acetaminophen) obtained in each of Examples 8 and 9 and Comparative Example 3 were administered to male beagle which had not been fed overnight (one group: 4 bodies of beagle), and blood was sampled after 1 hr, 2 hr, 3 hr, 4 hr, 5 hr, 6 hr, 8 hr, 10 hr, 12 hr, and 24 hr of the administration and the concentrations of acetaminophen in blood plasma were measured using high performance liquid chromatography (HPLC). The results are shown in FIG. 10.

In each of the capsule preparations, substantially the same change in the concentration in blood was exhibited until 5 hours after the administration. However, after 5 hours or later, in the preparation of Comparative Example 3, the concentration in blood could not be sustained, while, in the preparations of Examples 8 and 9, the concentration in blood was sustained at a high value even after 5 hours or later. From these results, it is found that, in the conventional sustained release preparation coated with a water-insoluble polymer, such as ethyl cellulose or the like, it is difficult to release the drug at the lower portion of a digestive tract having small moisture content to sustain the high concentration of the drug in blood, while, the multilayer-coated preparation of the present invention is able to release a drug effectively even at the lower portion of the digestive tract to sustain the high concentration of the drug in blood.

Further, since both of the preparations in Examples 8 and 9 have the above-described effect, it is found that the preparation of the present invention is applicable to various forms of preparations, such as fine particles, granule, and the like.

INDUSTRIAL APPLICABILITY

The multilayered coating layer in the preparation of the present invention has characteristic features such that it can efficiently suppress the releasing rate of the drug with a small coating ratio, without causing a phenomenon of reaching the upper limit of drug release, thereby making it possible to obtain easily a sustained release preparation of once a day taking type.

Therefore, even when the amount of a coating for suppressing the drug release cannot be increased despite of a high solubility of the drug in water, since it is necessary for the preparation to have a high drug content, or when it is difficult to suppress the drug release with a small coating ratio since the core substance has a particle diameter of as small as 50 to 200 µm, therefore having a large surface area per unit weight, by using the preparation of the present invention, a preparation of once a day taking type having a high drug content can be obtained. In addition, even when it is difficult to release all the drug contained in the preparation due to an extremely poor solubility of the drug, almost 100% of the drug in the preparation can be released with the preparation of the present invention.

Further, when the preparation of the present invention is orally administered, the multilayered coating layer undergoes erosion with the lapse of time (while the preparation moves through a digestive tract), and slowly becomes thinner. Therefore, it is possible to release the drug satisfactorily even at the lower portion of a digestive tract having small moisture content.

The invention claimed is:

1. A sustained release preparation which comprises:
a drug-containing core substance and
a multilayered coating layer covering said core substance, wherein all adjacent layers in said multilayered coating layer contain mutually different hydrophobic organic compound-water-soluble polymer mixtures; and
wherein said hydrophobic organic compound is one kind or two or more kinds selected from the group consisting of a higher fatty acid having 6 to 22 carbon atoms optionally having an unsaturated bond, a higher alcohol having 6 to 22 carbon atoms optionally having an unsaturated bond, a triglyceride of a higher fatty acid having 6 to 22 carbon atoms optionally having an unsaturated bond, and a natural fat and oil optionally hydrogenated, and said water-soluble polymer is one kind or two or more kinds selected from the group consisting of a water-soluble cellulose ether, a water-soluble vinyl derivative and an alkylene oxide polymer.

2. The sustained release preparation according to claim 1, wherein said higher fatty acid having 6 to 22 carbon atoms optionally having an unsaturated bond is stearic acid, lauric acid, myristic acid, palmitic acid or behenic acid, said higher alcohol having 6 to 22 carbon atoms optionally having an unsaturated bond is lauryl alcohol, myristyl alcohol, cetyl alcohol, stearyl alcohol or behenyl alcohol, said triglyceride of a higher fatty acid having 6 to 22 carbon atoms optionally having an unsaturated bond is stearic triglyceride, myristic triglyceride, palmitic triglyceride or lauric triglyceride, said natural fat and oil optionally hydrogenated is hydrogenated castor oil, hydrogenated coconut oil or beef tallow, said water-soluble cellulose ether is methyl cellulose, hydroxypropyl cellulose or hydroxypropyl methyl cellulose, said water-soluble vinyl derivative is polyvinyl pyrrolidone or polyvinyl alcohol, and said alkylene oxide polymer is polyethylene glycol.

3. The sustained release preparation according to claim 1, wherein said hydrophobic organic compound is stearic acid, and said water-soluble polymer is hydroxypropyl cellulose.

4. The sustained release preparation according to claim 1, wherein a content of the hydrophobic organic compound in said hydrophobic organic compound-water-soluble polymer mixture in each of the layers is within the range of 20 to 99.5% by weight.

5. The sustained release preparation according to claim 1, wherein an average particle size of said drug-containing core substance is 200 µm or less, and a content of said hydrophobic organic compound in said hydrophobic organic compound-water-soluble polymer mixture in each of the layers is within the range of 80 to 99.5% by weight.

6. The sustained release preparation according to claim 1, wherein an average particle size of said drug-containing core substance is 700 µm or more, and a content of said hydrophobic organic compound in said hydrophobic organic compound-water-soluble polymer mixture in each of the layers is within the range of 40 to 80% by weight.

7. The sustained release preparation according to claim 1, wherein all combinations of adjacent layers in said multilayered coating layer contain a hydrophobic organic compound-water-soluble polymer mixture wherein at least one kind of either said hydrophobic organic compound or said water-soluble polymer is mutually different.

8. The sustained release preparation according to any one of claims 1, 2 and 3, wherein all combinations of adjacent layers in said multilayered coating layer contain a hydrophobic organic compound-water-soluble polymer mixture wherein the kinds of said hydrophobic organic compound and said water-soluble polymer are the same, while the contents of said hydrophobic organic compound are mutually different.

9. The sustained release preparation according to claim 1, wherein some combinations of adjacent layers in said multilayered coating layer contain hydrophobic organic compound-water-soluble polymer mixtures wherein at least one of said hydrophobic organic compound or said water-soluble polymer is mutually different, while other combinations of adjacent layers contain hydrophobic organic compound-water-soluble polymer mixtures wherein the kinds of said hydrophobic organic compound and said water-soluble polymer are the same, while the contents of said hydrophobic organic compound are mutually different.

10. The sustained release preparation according to claim 8, wherein the difference in the contents of each combination of said hydrophobic organic compound in said hydrophobic organic compound-water-soluble polymer mixtures wherein the contents of said hydrophobic organic compound are mutually different is 5% by weight or more.

11. The sustained release preparation according claim 1, wherein combinations of said hydrophobic organic compound-water-soluble polymer mixtures contained in each combination of adjacent layers is single in said multilayered coating layer.

12. The sustained release preparation according to claim 1, wherein combinations of said hydrophobic organic compound-water-soluble polymer mixtures contained in each combination of adjacent layers are plural in said multilayered coating layer.

13. The sustained release preparation according to claim 1, wherein said multilayered coating layer is formed with layers all having the same coating ratio.

14. The sustained release preparation according to claim 1, wherein a number of layers contained in said multilayered coating layer is 4 to 50 layers, and a coating ratio of said multilayered coating layer is 10 to 150% by weight.

15. The sustained release preparation according to claim 1, wherein an undercoating layer to improve preparation strength is provided at the inside of said multilayered coating layer.

16. The sustained release preparation according to claim 15, wherein said undercoating layer comprises a water-insoluble polymer substance as a main component.

17. The sustained release preparation according to claim 16, wherein said undercoating layer comprises ethyl cellulose as a main component.

18. The sustained release preparation according to claim 15, wherein a coating ratio of said undercoating layer is 5 to 50% by weight.

19. A method of producing a sustained release preparation, having a multilayered coating layer wherein adjacent layers contain mutually different hydrophobic organic compound-water-soluble polymer mixtures, which comprises:
(a) spray-coating a solution containing a hydrophobic organic compound-water-soluble polymer mixture onto a drug-containing core substance,
(b) spray-coating a solution containing a different hydrophobic organic compound-water-soluble polymer mixture onto the resulting coating layer, and
(c) repeating coating step (b); and
wherein said hydrophobic organic compound is one kind or two or more kinds selected from the group consisting of a higher fatty acid having 6 to 22 carbon atoms optionally having an unsaturated bond, a higher alcohol having 6 to 22 carbon atoms optionally having an unsaturated bond, a triglyceride of a higher fatty acid having 6 to 22 carbon atoms optionally having an unsaturated bond, and a natural fat and oil optionally hydrogenated, and said water-soluble polymer is one kind or two or more kinds selected from the group consisting of a water-soluble cellulose ether, a water-soluble vinyl derivative and an alkylene oxide polymer.

20. The method of producing a sustained release preparation according to claim 19, wherein after providing an undercoating layer for improving preparation strength on said drug-containing core substance, a solution containing a hydrophobic organic compound-water-soluble polymer mixture is spray-coated.

21. The sustained release preparation according to claim 9, wherein the difference in the contents of said hydrophobic organic compound in each combination of said hydrophobic organic compound-water-soluble polymer mixtures wherein the contents of said hydrophobic organic compound are mutually different is 5% by weight or more.

* * * * *